United States Patent [19]
Mittleman

[11] 3,941,149
[45] Mar. 2, 1976

[54] VALVE
[75] Inventor: Herbert Mittleman, Deerfield, Ill.
[73] Assignee: Baxter Laboratories, Inc., Morton Grove, Ill.
[22] Filed: Nov. 11, 1974
[21] Appl. No.: 522,828

[52] U.S. Cl............................ 137/493.1; 137/525.1
[51] Int. Cl.² ........................................ F16K 15/14
[58] Field of Search............... 137/525, 525.1, 493.1

[56] References Cited
UNITED STATES PATENTS
| | | |
|---|---|---|
| 456,028 | 7/1891 | Foster............................ 137/525.1 |
| 3,159,176 | 12/1964 | Russell et al..................... 137/525.1 |

*Primary Examiner*—William R. Cline

[57] ABSTRACT

A duckbill-umbrella valve capable of resisting undesired flow is provided by a cylindrical elongated member defining a passageway and including converging flexible lips which are strengthened by a radially outward portion of the cylindrical elongated member surrounding the flexible lips.

3 Claims, 9 Drawing Figures

U.S. Patent  March 2, 1976  3,941,149
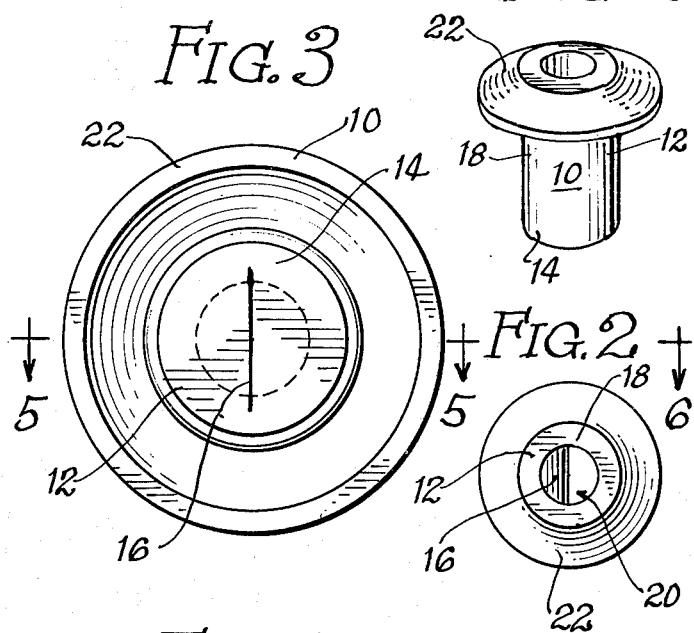
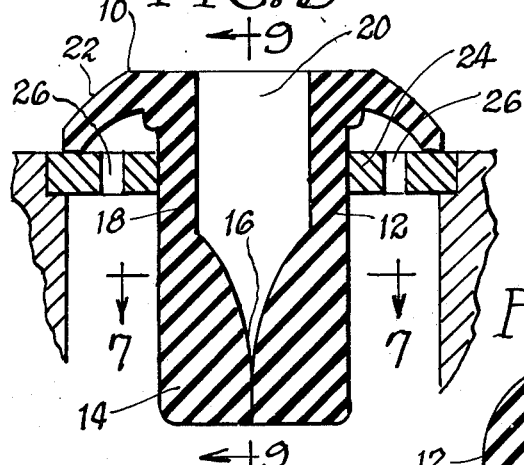
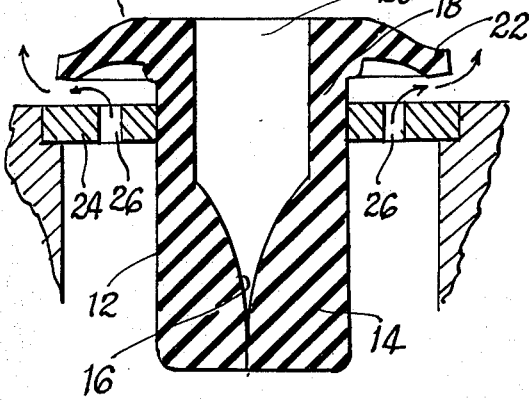
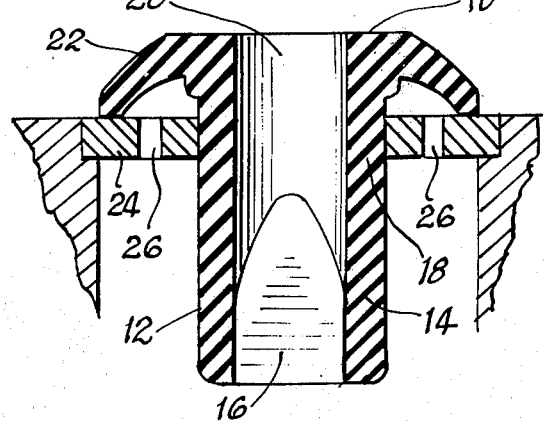

VALVE

BACKGROUND OF THE INVENTION

This invention relates to a flexible control valve, and more particularly, to a duckbill-umbrella valve for regulating fluid flow in each of two directions.

Duckbill valves, such as the type disclosed in U.S. Pat. No. 3,155,110 and U.S. Pat. No. 3,159,176, are well-known and generally operate effectively at relatively low pressures. At back pressures or head pressures below a desired opening pressure, however, the duckbill elements may spread apart causing undesired fluid flow.

In a typical operation of a fluid transfer device using a duckbill-umbrella valve, the umbrella portion of the valve regulates the flow of a primary solution of medicament to a pump or syringe. The duckbill elements regulate the flow of fluid transferred from the pump or syringe to the patient. When the syringe is raised or elevated to the desired position, a pressure head may build up and cause the duckbill elements to separate, thereby allowing undesired gravity flow of the syringe-fluid to the patient. When a relatively high pressure pump is used instead of the syringe, head pressures may be even greater. Excessive back pressures may develop, causing the duckbill elements to separate and allowing undesired backflow of fluid from the patient to the pump. Excessive back pressures may cause body fluids to be sucked out or withdrawn from the patient, and such withdrawal of body fluids from a patient without the supervision of a physician is extremely dangerous.

U.S. Pat. No. 3,710,942 illustrates a highly porous foam insert bonded to a duckbill valve. This construction is suggested as a means for providing additional biasing force to prevent the duckbill elements from opening until a certain pressure is reached. It has been found, however, that this type of valve is relatively expensive to manufacture. The density of the foam or sponge is difficult to control within a desired range, which results in the production of duckbill valves having different densities and which open at different pressures rather than one desired pressure. Furthermore, it is very difficult to control the radial dimension of the highly porous foam within a desired tolerance, which results in duckbill valves of different sizes.

In operation, the sponge or foam insert described in U.S. Pat. No. 3,710,942, may not provide sufficient biasing force to prevent the duckbill elements from opening at a pressure head as low as one psi. Furthermore, thick viscous solutions do not readily flow through the flow passageway of the valve.

When it is desirable to have a valve open at a predetermined pressure, such as 42 inches of water head, the previously described prior art valves may be ineffective causing undesired fluid flow at pressures as low as 36 inches of water head.

It is, therefore, an object of this invention to provide a duckbill-umbrella valve that operates satisfactorily to prevent flow until a predetermined amount of pressure is achieved.

Other objects of this invention are to provide a safety valve which is dependable in operation, relatively inexpensive to manufacture, easily installed and removed from operating position, and capable of performing properly after long periods of use.

These and other objects will become apparent from the following description and appended claims.

BRIEF DESCRIPTION OF THE INVENTION

In accordance with the present invention, there is provided an umbrella check valve including an elongated member defining a central passageway therethrough. A duckbill member is connected to, surrounded by and thus enclosed within the elongated member. The duckbill member includes a pair of lips normally closing the passageway for preventing transfer of fluid in an upward, or first, direction. The lips are flexibly responsive to a predetermined fluid pressure in a downward, or second, direction to open the passageway.

An umbrella portion extends from a portion of the elongated member spaced from the duckbill member. The umbrella portion normally checks fluid flow generally in the downward direction and is flexibly responsive to predetermined fluid pressure generally in the upward direction so as to permit fluid flow generally in the upward direction.

In the illustrative embodiment, the check valve is formed in a unitary molded construction.

A more detailed explanation of the invention is provided in the following description and claims, and is illustrated in the accompanying drawings.

BRIEF DESCRIPTION OF THE DRAWINGS

FIG. 1 is a perspective view of a duckbill-umbrella valve constructed in accordance with the principles of the present invention;

FIG. 2 is a top view thereof;

FIG. 3 is an enlarged bottom view thereof illustrating the lip member in the normally closed position;

FIG. 4 is an enlarged bottom view thereof illustrating the lip member in the open position;

FIG. 5 is a cross-sectional view, taken substantially along the plane of line 5—5 of FIG. 3, showing the lip member in the normally closed position;

FIG. 6 is a cross-sectional view, taken substantially along the plane of line 6—6 of FIG. 4, depicting the operable direction of fluid flow through the flow passageway of the valve and showing the converging lip member in an open position;

FIG. 7 is a cross-sectional view taken substantially along the plane of line 7—7 of FIG. 5;

FIG. 8 is a cross-sectional view similar to FIG. 5, illustrating flexing of the umbrella portion to permit fluid flow in the opposite direction; and FIG. 9 is a cross-sectional view taken along the plane of line 9—9 of FIG. 5.

DETAILED DESCRIPTION OF THE ILLUSTRATIVE EMBODIMENT

Referring to the figures of the drawings, a generally mushroom-shaped duckbill-umbrella valve 10, which may operate as a check and relief valve, is formed of an elastic or resilient material, such as but not limited to rubber, including latex, synthetic rubber, silicone rubber, or plastic having the characteristics of rubber. Valve 10 includes an elongated member 12 having a generally cylindrical configuration. Elongated member 12 includes a lower portion 14 forming a generally cylindrical leg and having an internal flexible converging member 16. Elongated member 12 also includes an upper portion 18 above converging member 16. Elongated member 12 defines a central longitudinal aperture or fluid-flow passageway 20. A flexible annular umbrella portion 22 extends from upper portion 18 and it may seat against a fluid-restraining member 24 covering one or more fluid passageways 26 defined by fluid-restraining member 24.

Lower portion 14 is preferably formed integrally with and is aligned longitudinally with upper portion 18. If desired, lower portion 14 may be tapered radially inwardly to permit easy insertion of elongated member 12 in an aperture defined by fluid-restraining member 24. Furthermore, the radial outer edge of lower portion 14 may be rounded or chamfered to permit elongated member 12 to easily enter an aperture defined by fluid-restraining member 24.

Converging member 16 comprises a pair of lips having a "duckbill" configuration. Converging member 16 is biased radially inwardly so that the lips normally press against each other to prevent the flow of fluid through flow-passageway 20. Lips 16 are generally V-shaped and flex radially outward in response to a predetermined pressure head to open flow-passageway 20. Member 16 converges in the direction of desired flow. In an alternative embodiment, converging member 16 may be shaped to form a circular converging portion or cone having an aperture or longitudinal slit in the bottom thereof and biased or pinched inwardly to normally close flow-passageway 20. In this alternative embodiment member 16 forms a converging nozzle having an internal configuration substantially as shown in FIG. 5 and which is normally biased to close flow-passageway 20, but which will open or spread apart in response to a predetermined pressure head to permit the passage of fluid therethrough.

Lower portion 14 strengthens and rigidifies converging member 16 by reducing its flexibility. This makes it more difficult to separate member 16. Because lower portion 14 is stronger and more rigid than certain prior art valves, lips 16 will not open or yield at pressures below a predetermined amount. Thus portion 14, which extends radially outward from lips 16, serves to bias converging member 16 in a normally closed position to a far greater extent than if portion 14 were not present.

It may also be appreciated that the entire valve 10 may be formed of a unitary molded construction, for economy in manufacture.

In operation, flow-passageway 20 is normally closed by converging member 16 to prevent the flow of fluid in an upward direction. When the pressure in the downward direction exceeds a predetermined amount, lips 16 will open and spread apart permitting fluid to flow downwardly therethrough. Umbrella portion 22 is normally seated against fluid-restraining member 24 to prevent fluid from flowing downwardly through fluid-passageway 26. When the fluid pressure in the upward direction exceeds a predetermined amount, umbrella portion 22 will flex to permit fluid to flow upward around the periphery of the umbrella 24. The fluid being checked and released by flexible umbrella portion 22 may, but need not be, the same as the fluid passing through flow-passageway 20.

The valve described in this invention may be used in fluid transfer devices of the type described in pending U.S. application, Ser. No. 463,221, filed Apr. 23, 1974, and assigned to the Assignee of the present invention. The valve of the present invention may also be used in master cylinder brake applications and in various other applications, such as the relief of excess fuel vapor pressure in small, high-speed gasoline engines such as used with outboard motors and chain saws and the like. The valve of the present invention may be used in hydraulic brake systems or in other fields where it is desired to permit flow of fluid in one direction, but to prevent it from flowing in the opposite direction and where a flow or relief action in the opposite direction must be provided. Thus, it can be seen that the converging member portion of this invention is of sufficient rigidity to avoid being opened upon a head pressure or back pressure below a predetermined amount.

Although an embodiment of the invention has been shown and described, it is to be understood that various modifications and substitutions may be made by those skilled in the art without departing from the novel spirit and scope of the invention.

What is claimed is:

1. A unitary valve comprising, in combination: a generally cylindrical elongated member defining a central passageway therethrough, said elongated member integrally including an internal duckbill lips configuration with said duckbill lips extending radially inward to normally close said passageway for preventing transfer of fluid in a first direction and said lips being responsive to a predetermined fluid pressure in a second direction to open said passageway, said elongated member having an open bore at one end which open bore extends through a portion of said elongated member toward its opposite end, said elongated member having said duckbill lips closure formed at said opposite end, said elongated member having a substantially greater material thickness at said opposite end than at the portion thereof adjacent said bore, said greater material thickness operating to bias said duckbill lips together to prevent said duckbill from opening in response to a pressure below said predetermined pressure; and an annular umbrella portion integrally extending from said elongated member, normally checking fluid flow generally in said second direction, and flexibly responsive to a predetermined fluid pressure generally in said first direction to allow fluid flow generally in said first direction.

2. A unitary valve as described in claim 1, wherein said valve is formed in a unitary molded construction.

3. A unitary valve as described in claim 1, wherein said generally cylindrical elongated member has a substantially circular cross-sectional configuration.

* * * * *